US 6,563,002 B2

(12) United States Patent
Iino et al.

(10) Patent No.: US 6,563,002 B2
(45) Date of Patent: May 13, 2003

(54) BISCYCLOPROPANECARBOXAMIDE COMPOUNDS AND PHARMACEUTICAL USE THEREOF

(75) Inventors: Yukio Iino, Kawasaki (JP); Kohichi Fujita, Kawasaki (JP); Takashi Yamamoto, Kawasaki (JP); Kenji Takehana, Kawasaki (JP); Tsuyoshi Kobayashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/085,073

(22) Filed: Mar. 1, 2002

(65) Prior Publication Data

US 2002/0161053 A1 Oct. 31, 2002

Related U.S. Application Data

(63) Continuation of application No. PCT/JP00/05914, filed on Aug. 31, 2000.

(30) Foreign Application Priority Data

Sep. 1, 1999 (JP) ............................................. 11-247483

(51) Int. Cl.[7] ..................... C07C 233/57; C07C 233/58; C07C 233/60; C07C 233/61; C07C 233/62
(52) U.S. Cl. .................. 564/155; 564/154; 564/157; 564/158; 546/308; 514/352; 514/616
(58) Field of Search ................... 514/352, 616; 546/308; 564/154, 155, 157, 158

(56) References Cited

U.S. PATENT DOCUMENTS 4,975,459 A * 12/1990 Mehta et al. ............... 514/475

FOREIGN PATENT DOCUMENTS

| GB | 2239012 | 6/1991 |
|---|---|---|
| JP | 2000-169479 | 6/2000 |
| WO | 99/61013 | 12/1999 |
| WO | 00/15603 | 3/2000 |

* cited by examiner

*Primary Examiner*—Brian Davis
(74) *Attorney, Agent, or Firm*—Oblon, Spivak, McClelland, Maier & Neustadt, P.C.

(57) ABSTRACT

The present invention discloses biscyclopropanecarboxamide compounds and pharmaceutically acceptable salts thereof; and also NF-kappa B activation inhibitors, Inflammatory cytokine production inhibitors, matrix metalloprotease production inhibitors, inflammatory cell adhesion molecules incidence inhibitors, antiinflammatory agents, antirheumatic agents, immunosuppressive agents, cancerous metastasis inhibitors or antiviral agents each containing such a compound as the active ingredient.

17 Claims, No Drawings

BISCYCLOPROPANECARBOXAMIDE COMPOUNDS AND PHARMACEUTICAL USE THEREOF

This application is a Continuation of International application PCT/JP00/05914 Filed on Aug. 31, 2000.

BACKGROUND OF THE INVENTION

The present invention relates to agents for treating various inflammatory diseases:

It is known that various inflammatory diseases, rheumatism, immunoreactive diseases, cancerous metastasis and viral diseases are caused by the abnormal production of inflammatory cytokines or matrix metalloproteases or by an increase in the incidence of inflammatory cell adhesion molecules. Although various medicines for these diseases have been developed, the development of a highly safe medicine having a higher medicinal effect and only slight side effects is demanded.

It is supposed that various chronic inflammatory diseases are caused because inflammatory mediators such as various cytokines (in particular, IL-1, IL-2, IL-6, IL-8, TNF, etc. for inflammatory diseases), adhesion molecules and tissue destroying enzymes (such as matrix metalloproteases) are continuously produced by the continuous extracellular stimulation.

These inflammatory mediators are produced because the gene expression is activated by the extracellular stimulation. In this step, a transcription factor (TF) known as NF-kappa B plays the most important role. If the activation of NF-kappa B can be inhibited, the increase and chronicity of the inflammation can be prevented. This method will be a hopeful therapeutic method for inflammatory diseases such as rheumatoid arthritis and various autoimmune diseases.

Glucocorticoid hormone (GC) which strongly inhibits the activation of NF-kappa B in the cells is practically used as a powerful antiinflammatory agent or immunosuppressive agent. However, GC has various side effects caused by hormonal action thereof, and it also causes rebound phenomena. Therefore, the use of GC as a medicine is limited at present.

DISCLOSURE OF THE INVENTION

An object of the present invention is to provide new compounds having a high medicinal effect and less side effects and useful for the treatment of chronic inflammatory diseases.

Another object of the present invention is to provide a pharmaceutical composition containing the compound(s).

Still another object of the present invention is to provide an inflammatory cytokine production inhibitor, a matrix metalloprotease production inhibitor or an inhibitor of incidence of inflammatory cell adhesion molecules, each of which contains the above-described compound(s) as the active ingredient.

A further object of the present invention is to provide an antiinflammatory agent, an antirheumatic agent, an immunosuppressive agent, a cancerous metastasis inhibitor or an antiviral agent, each of which contains the above-described compound(s) as the active ingredient.

After intensive investigations made for the purpose of obtaining compounds having a strong activity of inhibiting NF-kappa B activation and useful as agents for treating chronic inflammatory diseases, the inventors have found compounds represented by general formula (I). The present invention has been completed on the basis of this finding.

Namely, the present invention provides biscyclopropanecarboxamide compounds represented by the following general formula (I) and pharmaceutically acceptable salts thereof:

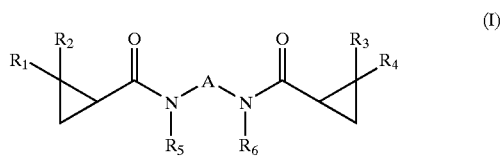

wherein $R_1$ to $R_4$, which may be the same or different from each other, each represent methyl group or chlorine atom, $R_5$ and $R_6$, which may be the same or different from each other, each represent hydrogen atom, an alkyl group having 1 to 6 carbon atoms or an aryl group which may have a substituent (s), and —A— represents one of the groups of the following general formulae (II), (III), (IV) and (V):

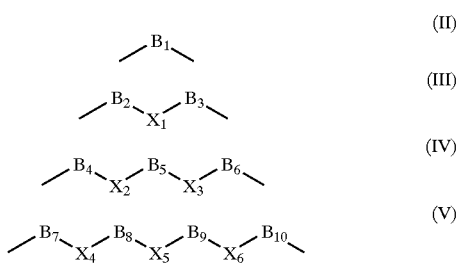

wherein $B_1$ to $B_{10}$, which may be the same or different from each other, each represent an aromatic ring which may have a substituent(s) or an aromatic heterocyclic group having at least one hetero atom, which may have a substituent(s), —$X_1$— to —$X_6$—, which may be the same or different from each other, each represent an interatomic bond, —O—, —$NR_7$—, —$CR_8R_9$—, —S—, —SO—, —$SO_2$—, —CO—, —O—CO—, —CO—O—, —$NR_{10}$—CO— or —CO—$NR_{11}$—wherein $R_7$ represents hydrogen atom, an alkyl group having 1 to 6 carbon atoms or an acyl group having 1 to 6 carbon atoms, $R_8$ to $R_9$ each represent hydrogen atom, hydroxyl group, a halogen atom, an alkyl group having 1 to 6 carbon atoms or an alkoxyl group having 1 to 6 carbon atoms, and $R_{10}$ to $R_{11}$ each represent hydrogen atom or an alkyl group having 1 to 6 carbon atoms.

The present invention also provides a pharmaceutical composition containing the above-described biscyclopropanecarboxamide compound(s) or pharmaceutically acceptable salt(s) thereof.

The present invention provides NF-kappa B activation inhibitors, inflammatory cytokine production inhibitors, matrix metalloprotease production inhibitors and inhibitors of incidence of inflammatory cell adhesion molecules containing the above-described biscyclopropanecarboxamide compound(s) or pharmaceutically acceptable salt(s) thereof as the active ingredient. They are each usable as an antiinflammatory agent, an antirheumatic agent, an immunosuppressive agent, a cancerous metastasis inhibitor or an antiviral agent.

When —A— in the above-described compounds is benzene ring having a substituent, the biscyclopropanecarboxamide compounds or pharmaceutically acceptable salts thereof exhibit an excellent effect.

BEST MODE FOR CARRYING OUT THE INVENTION

The detailed description will be made below on the present invention.

The term "alkyl groups" in the present invention indicates linear or branched alkyl groups having 1 to 6 carbon atoms such as methyl group, ethyl group, n-propyl group, isopropyl group, n-butyl group, isobutyl group, sec-butyl group, tert-butyl group, n-pentyl group, isopentyl group, tert-pentyl group, neopentyl group, 2-pentyl group, 3-pentyl group, n-hexyl group and 2-hexyl group. Methyl group, ethyl group, etc. are preferred.

The term "acyl groups" indicates linear or branched acyl groups having 1 to 6 carbon atoms or acyl groups having an aryl group, which may be substituted, such as formyl group, acetyl group, propionyl group, butyroyl group, isobutyroyl group, valeroyl group, isovaleroyl group, pivaloyl group, hexanoyl group, acryloyl group, methacryloyl group, crotonoyl group, isocrotonoyl group, benzoyl group and naphthoyl group.

The aryl groups include, for example, phenyl group, indenyl group, naphthyl group and fluorenyl group. Phenyl group is preferred.

The halogen atoms are, for example, fluorine atom, chlorine atom, bromine atom and iodine atom.

The alkoxyl groups are linear or branched alkoxyl groups having 1 to 6 carbon atoms such as methoxyl group, ethoxyl group, n-propoxyl group, isopropoxyl group, n-butoxyl group, isobutoxyl group, sec-butoxyl group and tert-butoxyl group. Methoxyl group, ethoxyl group, etc. are preferred.

The term "aromatic ring" in the definition of $B_1$ to $B_{10}$ includes, for example, benzene, indene, naphthalene and fluorene. Benzene is preferred.

The term "an aromatic heterocyclic ring having at least one hetero atom" in the definition of $B_1$ to $B_{10}$ means a 5- to 7-membered aromatic heterocyclic ring composed of carbon and nitrogen, oxygen, sulfur or selenium. They are, for example, pyridine, dihydropyran, pyridazine, pyrimidine, pyrazine, triazine, tetrazine, pyrrole, furan, thiophene, oxazole, isoxazole, thiazole, isothiazole, imidazole, triazole, pyrazole, furazane and thiadiazole.

The expression "which may have a substituent(s)" in "an aromatic ring which may have a substituent(s)" and "an aromatic heterocyclic group having at least one hetero atom, which may have a substituent(s)" in $B_1$ to $B_{10}$ indicates that the aromatic ring or the aromatic heterocyclic group may have 1 to 3 substituents which may be the same or different from each other and that the positions of the substituents are not particularly limited. Examples of them are halogen atoms, alkyl groups which may have a substituent(s), hydroxyl group, alkoxyl groups, carboxyl group, alkoxycarbonyl groups, cyano group, aralkyl groups which may have a substituent(s) on the alkyl chain or on the aryl group, and amino group which may be substituted with an amino-protecting group(s).

The alkoxycarbonyl groups are, for example, methoxycarbonyl group, ethoxycarbonyl group, propoxycarbonyl group, isopropoxycarbonyl group, n-butoxycarbonyl group, isobutoxycarbonyl group, sec-butoxycarbonyl group and tert-butoxycarbonyl group.

The aralkyl groups are, for example, benzyl group, phenethyl group and phenylpropyl group.

The type of the substitution in $B_1$ to $B_{10}$ is not particularly limited. For example, when $B_1$ to $B_{10}$ are benzene or pyridine, any of the ortho-substitution, meta-substitution and para-substitution is possible.

In general formula (1), $R_1$ to $R_4$ is preferably methyl group.

$R_5$ and $R_6$ are each preferably hydrogen atom.

—A— is preferably represented by general formula (II), (IV) or (V).

—A— is also preferably represented by the following general formula (VI), or (VII).

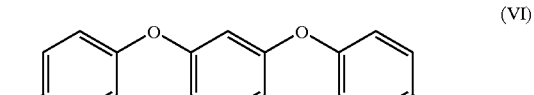

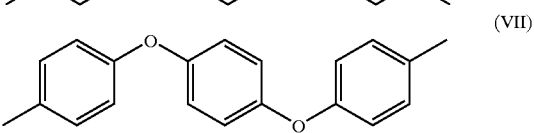

Preferably, $R_5$ and $R_6$ in general formula (I) are each hydrogen atom, and $B_1$, $B_2$, $B_4$ and $B_7$ in general formulae (II), (III), (IV) and (V) are each benzene ring which may have a substituent(s).

It is also preferred that $R_5$ and $R_6$ in general formula (I) are each hydrogen atom, and $B_1$ to $B_{10}$ in general formulae (II), (III), (IV) and (V) are each benzene ring which may have a substituent(s).

It is also preferred that $R_5$ and $R_6$ in general formula (I) are each hydrogen atom, and —A— is represented by general formulae (VI) or (VII).

It is also preferred that $R_5$ and $R_6$ in general formula (I) are each hydrogen atom, and —A— is benzene ring which may have a substituent(s).

It is also preferred that $R_1$ to $R_4$ in general formula (I) are each methyl group, $R_5$ and $R_6$ are each hydrogen atom and —A— is benzene ring having a substituent(s).

It is also preferred that the absolute configuration of the two carbon atoms each connected to the carbonyl group on the cyclopropyl group in general formula (I) is S.

It is also preferred that the absolute configuration of the two carbon atoms each connected to the carbonyl group on the cyclopropyl group in general formula (I) is R.

When the compounds of the present invention are sufficiently acidic, the pharmaceutically acceptable salts herein indicate ammonium salts of them and also salts of them with alkali metals (preferably such as sodium and potassium), alkaline earth metals (preferably such as calcium and magnesium), and organic bases such as amino acids, e.g. dicyclohexylamine, benzathine, N-methyl-D-glucan, hydramine and amino acids including arginine, lysine, etc. When the compounds of the present invention are sufficiently alkaline, the pharmaceutically acceptable salts herein indicate acid-addition salts of them such as salts of them with inorganic acids, e.g. hydrochloric acid, sulfuric acid, nitric acid and phosphoric acid, and salts of them with organic acids, e.g. acetic acid, lactic acid, citric acid, tartaric acid, maleic acid, fumaric acid and monomethylsulfuric acid. These salts may be hydrous salts or hydrates of them in some cases.

In the present invention all the isomers such as optical isomers and geometrical isomers, hydrates, solvates and crystal isomers are included.

The compounds of the present invention can be synthesized by methods described below.

For example, in the present invention, compounds of the formula (I) wherein A represents benzene ring and both ends thereof have the same structure can be obtained by synthesizing a corresponding diamine compound and then reacting the obtained compound with a corresponding equivalents (at least 2 equivalents) of an acid halide such as an acid chloride in the presence of a base, or with a corresponding equivalents (at least 2 equivalents) of a carboxylic acid in the presence of a condensing agent as shown below:

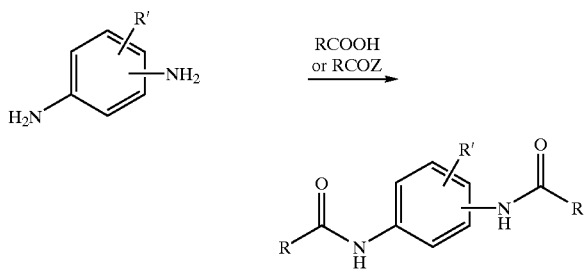

wherein R represents dimethylcyclopropyl group or dichlorocyclopropyl group, and Z represents a halogen atom.

By this reaction, for example, the following compound of the present invention can be synthesized:

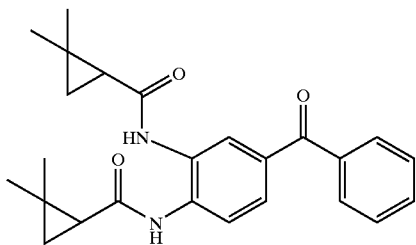

Further, the following compound can be synthesized by reducing the compound thus obtained:

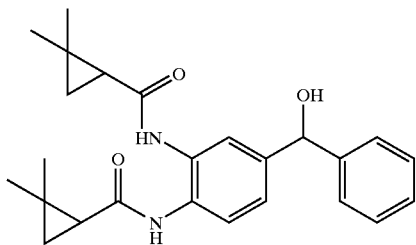

The compounds of the present invention can be synthesized according to these processes or by an ordinary method.

The compounds of the present invention obtained by the above-described process can be purified by a method usually employed in the organic synthesis such as extraction, distillation, crystallization or column chromatography.

The compounds of the present invention thus obtained have an activity of inhibiting the activation of NF-kappa B, and they are useful for the treatment of inflammatory diseases caused by such a transcription factor. Namely, they are useful as antiinflammatory agents, antirheumatic agents, immunosuppressive agents, cancerous metastasis inhibitors or antiviral agents capable of inhibiting the transcription of genes of inflammatory cytokines, matrix metalloproteases, inflammatory cell adhesion molecules, etc. and having no side effects such as hormonal effects.

When the compounds of the present invention are used as antiinflammatory agents, they can be administered to patients orally, intravenously or percutaneously or in the form of eye drops. The dose which varies depending on the symptoms and age of the patient and the administration method is usually 1 to 3,000 mg/kg/day.

The compounds of the present invention can be formulated by an ordinary method. The dosage forms are, for example, injections, tablets, granules, fine granules, powders, capsules, creams and suppositories. Pharmaceutical carriers include, for example, lactose, glucose, D-mannitol, starch, crystalline cellulose, calcium carbonate, kaolin, starch, gelatin, hydroxypropyl cellulose, hydroxypropylmethyl cellulose, polyvinylpyrrolidone, ethanol, carboxymethyl cellulose, calcium salt of carboxymethyl cellulose, magnesium stearate, talc, acetyl cellulose, white sugar, titanium oxide, benzoic acid, para-hydroxybenzoic acid esters, sodium dehydroacetate, gum arabic, tragacanth, methyl cellulose, egg yolk, surfactants, white sugar, simple syrup, citric acid, distilled water, ethanol, glycerol, propylene glycol, macrogol, disodium hydrogenphosphate, sodium dihydrogenphosphate, sodium phosphate, glucose, sodium chloride, phenol, thimerosal, para-hydroxybenzoic acid esters and sodium hydrogensulfite. They are mixed with the compounds of the present invention depending on the dosage form.

The amount of the active ingredient of the present invention contained in the preparation of the present invention varies in a wide range depending on the dosage form, and it is not particularly limited. Usually, the amount of the active ingredient is 0.01 to 100% by weight, preferably 1 to 100% by weight, based on the whole composition.

EXAMPLES

The following Examples will further illustrate the present invention, which by no means limit the invention.

Compounds synthesized in Examples 1 to 12 were as follows:

Compound of Example 1

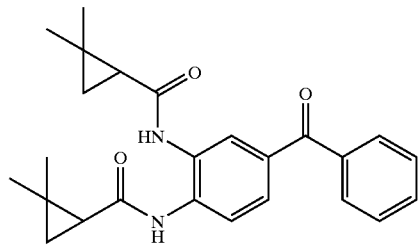

Compound of Example 2

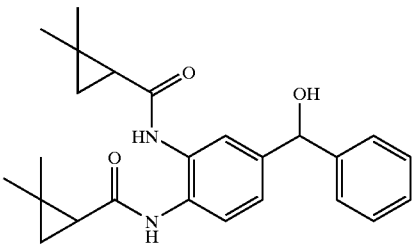

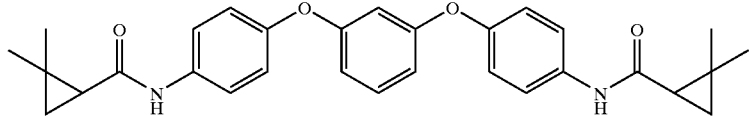
Compound of Example 3
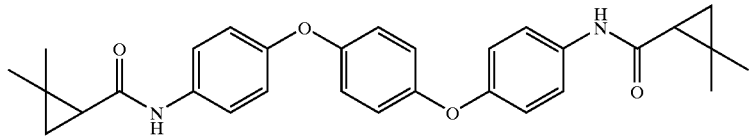
Compound of Example 4
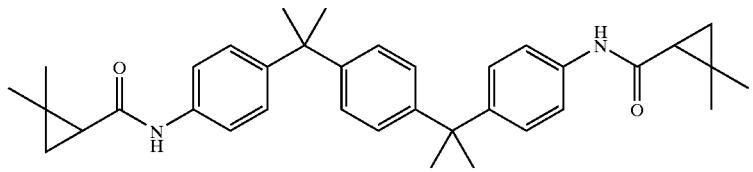
Compound of Example 5
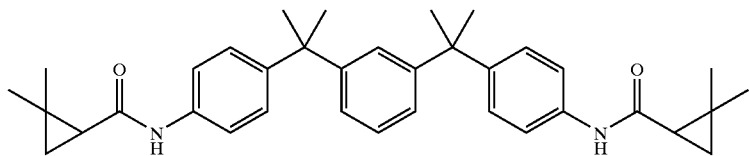
Compound of Example 6
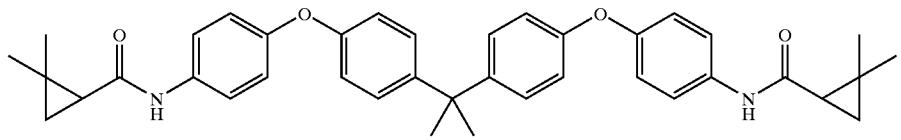
Compound of Example 7
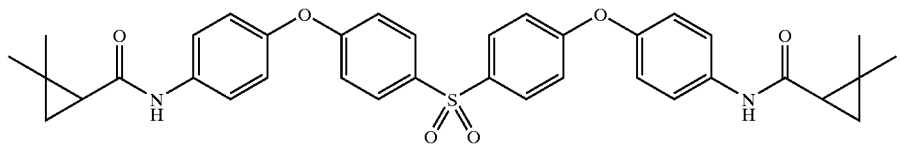
Compound of Example 8
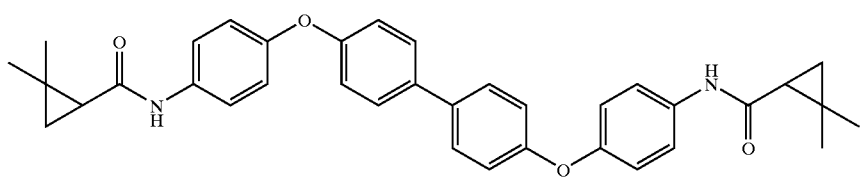
Compound of Example 9
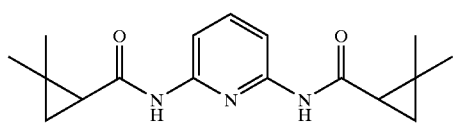
Compound of Example 10
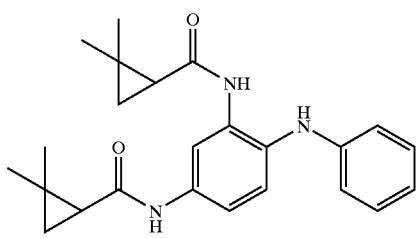
Compound of Example 11

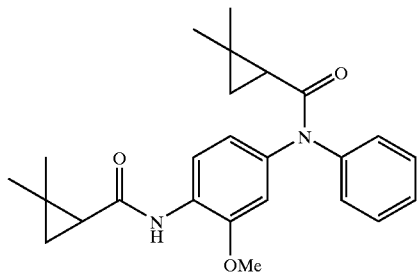

Compound of Example 12

Example 1

A solution of dimethylcyclopropanecarbonyl chloride (1.59 g, 12 mmol) in dichloromethane (5 ml) was slowly added to a solution of 3,4-diaminobenzophenone (1.06 g, 5 mmol) and triethylamine (2.02 g, 20 mmol) in a mixture of dichloromethane (10 ml) and dioxane (3 ml), and they were stirred at room temperature for 10 minutes. After the completion of the reaction, triethylamine hydrochloride thus precipitated was filtered out, and the solution was evaporated under reduced pressure. After the extraction with ethyl acetate, the obtained extract was washed with saturated sodium hydrogencarbonate solution, then with 2 N hydrochloric acid and then with saturated aqueous sodium chloride solution, dried over anhydrous sodium sulfate and concentrated under reduced pressure. The obtained oily product was purified by the silica gel column chromatography (hexane/ethyl acetate=1/1) to obtain the compound of Example 1 in the form of yellow crystals (1.63 g, 80%).

$^1$H NMR(300 MHz, CDCl$_3$) δ=0.80–0.90(2H, m), 1.15–1.30(14H, m), 1.40–1.60(2H, m), 7.45(2H, t, J=8.7 Hz), 7.55–7.65(2H, m), 7.70–7.80(4H, m), 8.15(1H, broad s), 8.80(1H, broad s). MS(ESI) m/z 405(MH$^+$).

Example 2

Sodium borohydride (160 mg, 4.2 mmol) was added to a solution of the compound obtained in Example 1 (1.4 g, 3.5 mmol) in ethanol (20 ml), and they were stirred at room temperature for 1 hour. After the completion of the reaction, the solvent was evaporated under reduced pressure. The obtained product was extracted with ethyl acetate, washed with 1 N hydrochloric acid and then with saturated sodium hydrogencarbonate solution, dried over anhydrous sodium sulfate and concentrated under reduced pressure. The obtained oily product was purified by the silica gel column chromatography (hexane/ethyl acetate) to obtain the compound of Example 2 in the form of yellow crystals (1.01 g, 70%)

$^1$H NMR(300 MHz, DMSO) δ=0.80–0.90(2H, m), 0.90–0.95(2H, m), 1.10–1.20(12H, m), 1.50–1.70(2H, m), 5.63(1H, d, J=3.9 Hz), 5.85(1H, d, J=3.9 Hz), 7.06–7.50(8H, m), 9.45(1H, broad s), 9.62(1H, broad s). MS(ESI) m/z 407(MH$^+$)

Example 3

The compound of Example 3 was synthesized from 1,3-bis(4-aminophenoxy)benzene in the same manner as that of Example 1.

$^1$H NMR(300 MHz, CDCl$_3$) δ=0.83(2H, dd, J=4.8, 7.8 Hz), 1.18–1.26(14H, m), 1.41(2H, dd, J=5.1, 7.8 Hz), 6.56–6.65(3H, m), 6.95(4H, d, J=9.0 Hz), 7.19(1H, t, J=5.2 Hz), 7.46(4H, d, J=8.4 Hz), 7.55(2H, s).

Example 4

The compound of Example 4 was synthesized from 1,4-bis(4-aminophenoxy)benzene in the same manner as that of Example 1.

$^1$H NMR(300 MHz, DMSO) δ=0.75(2H, dd, J=3.9, 8.1 Hz), 0.95(2H, dd, J=4.8, 4.8 Hz), 1.12(6H, s), 1.14(6H, s), 1.62(2H, dd, J=5.7, 7.8 Hz), 6.91–6.96(8H, m), 7.57(4H, d, J=9.0 Hz), 10.05(2H, s). MS(ESI) m/z 485 (MH$^+$)

Example 5

The compound of Example 5 was synthesized from α,α'-bis(4-aminophenyl)-1,4-diisopropylbenzene in the same manner as that of Example 1.

$^1$H NMR(300 MHz, CDCl$_3$) δ=0.82(2H, dd, J=4.2, 7.5 Hz), 1.18–1.28(14H, m), 1.38(2H, dd, J=6.0, 8.4 Hz), 1.63 (12H, s), 7.08(4H, s), 7.16(4H, d, J=8.7 Hz), 7.36(4H, d, J=8.7 Hz). MS(ESI) m/z 537 (MH$^+$).

Example 6

The compound of Example 6 was synthesized from 4,4'-(1,3-phenylenediisopropylidene)bisaniline in the same manner as that of Example 1.

$^1$H NMR(300 MHz, CDCl$_3$) δ=0.83(2H, dd, J=4.4, 8.2 Hz), 1.00(2H, dd, J=5.5, 8.2 Hz), 1.21–1.28(12H, m), 1.48 (2H, m), 1.51(3H, s), 1.58(3H, s), 6.63(2H, m), 7.00(4H, m), 7.13–7.29(6H, m), 7.69(2H, d, J=9.9 Hz). MS(ESI) m/z 537 (MH$^+$).

Example 7

The compound of Example 7 was synthesized from 2,2-bis[4-(4-aminophenoxy)phenyl]propane in the same manner as that of Example 1.

$^1$H NMR(300 MHz, CDCl$_3$) δ=0.84(2H, dd, J=4.2, 7.8 Hz), 1.02(2H, dd, J=4.3, 8.6 Hz), 1.20–1.28(12H, m), 1.39 (2H, dd, J=5.1, 8.4 Hz), 1.66(6H, s), 6.86(4H, d, J=8.7 Hz), 6.97(4H, d, J=8.7 Hz), 7.16(4H, d, J=8.7 Hz), 7.30(2H, s), 7.46(4H, d, J=8.7 Hz). MS(ESI) m/z 603 (MH$^+$).

Example 8

The compound of Example 8 was synthesized from bis[4-(4-aminophenoxy)phenyl]sulfone in the same manner as that of Example 1.

$^1$H NMR(300 MHz, CDCl$_3$) δ=0.83(2H, dd, J=4.5, 7.8 Hz), 1.02(2H, dd, J=4.8, 7.8 Hz), 1.18–1.21(12H, m), 1.38 (2H, dd, J=5.1, 7.8 Hz), 6.75(2H, m), 7.00(4H, d, J=9.0 Hz), 7.29(4H, d, J=6.0 Hz), 7.37(2H, s), 7.43(2H, s), 7.84(4H, d, J=6.9 Hz). MS(ESI) m/z 625 (MH$^+$).

Example 9

The compound of Example 9 was synthesized from 4,4'-bis(4-aminophenoxy)biphenyl in the same manner as that of Example 1.

$^1$H NMR(300 MHz, DMSO) δ=0.76(2H, dd, J=3.9, 7.1 Hz), 0.96(2H, dd, J=5.1, 5.1 Hz), 1.13(6H, s), 1.15(6H, s), 1.63(2H, dd, J=5.7, 7.8 Hz), 6.99(8H, d, J=8.4 Hz), 7.60(8H, m). MS(ESI) m/z 561 (MH$^+$).

Example 10

The compound of Example 10 was synthesized from 2,6-diaminopyridine in the same manner as that of Example 1.

$^1$H NMR(300 MHz, CDCl$_3$) δ=0.87(1H, dd, J=4.5, 7.8 Hz), 1.19–1.28(7H, m), 1.44(1H, m), 7.67(1H, t, J=8.1 Hz), 7.85(2H, s). MS(ESI) m/z 302 (MH).

Example 11

The compound of Example 11 was synthesized from 2,4-diaminodiphenylamine in the same manner as that of Example 1.

$^1$H NMR(300 MHz, CDCl$_3$) δ=0.81(2H, m), 1.10–1.26 (14H, m), 1.35(2H, m), 5.43(1H, s), 6.72(2H, d, J=8.8 Hz), 6.93(1H, t, J=6.3 Hz), 7.29(3H, m), 7.36(1H, s), 7.53(1H, s), 7.85(1H, s), 8.07(1H, s). MS(ESI) m/z 390 (M–H).

Example 12

The compound of Example 12 was synthesized from 4-amino-3-methoxydiphenylamine in the same manner as that of Example 1.

$^1$H NMR(300 MHz, CDCl$_3$) δ=0.68(1H, dd, J=6.9, 10.2 Hz), 0.84(1H, dd, J=4.8, 8.1 Hz), 0.95(3H, s), 1.20–1.30 (12H, m), 1.44(1H, dd, J=7.2, 13.2 Hz), 3.85(3H, s), 6.67 (2H, m), 6.95(1H, t, J=4.5 Hz), 7.07(2H, d, J=4.0 Hz), 7.22–7.36(2H, m),7.85(1H, s), 8.37(1H, s). MS(ESI) m/z 407 (MH$^+$).

Example 13

Evaluation of Inhibition of NF-Kappa B:

Cells used in the tests were obtained by stably introducing E. coli β-galactosidase (β-gal) genes into human normal umbilical vein endothelial cells (HUVEC) immortalized with SV 40 large T antigen. The genes were those driven by SV40 minimum promoter fused with 6 times of the NF-kappa B binding motif derived, from immunoglobulin kappa light-chain enhancer. The cells were subcultured in RPMI medium containing 10% of FBS, and spread on 96-well plates in a concentration of 1×10$^4$/well the day before the initiation of the experiments. The compound of the present invention was dissolved in DMSO in a suitable concentration and fed into the 96-well plates so that the final concentration of DMSO would be not higher than 1%. 30 minutes after the addition of the compound, NF-kappa B activity was induced with 1 ng/ml of IL-1β in each well. The β-gal activity was determined 16 hours after. The β-gal activity was determined with a chemical photogenic substrate (Galacton-Light-Plus: Boehringer Mannheim) according to the protocol attached to the reagent. A Luminescence detector (ATTO) was used for the determination, In this evaluation system, the β-gal activity derived with IL-1β was almost completely inhibited by glucocorticoid which is a known NF-kappa B inhibitor.

The results of the evaluation are shown in Table 1.

TABLE 1

| Example | NFkB inhibiting activity IC50 (ug/ml) |
|---------|---------------------------------------|
| 2       | 1                                     |
| 3       | 1.5                                   |
| 4       | 4                                     |

It is apparent from the above-described results that the compounds of the present invention have the activity of inhibiting the activation of NF-kappa B, and they are useful for the treatment of inflammatory diseases caused by such a transcription factor. Namely, they inhibit the transcription of genes of inflammatory cytokines, matrix metalloproteases and inflammatory cell adhesion molecules and they are useful as antiinflammatory agents, antirheumatic agents, immunosuppressive agents, cancerous metastasis inhibitors or antiviral agents.

What is claimed is:

1. Biscyclopropanecarboxamide compounds represented by the following general formula (I) and pharmaceutically acceptable salts thereof:

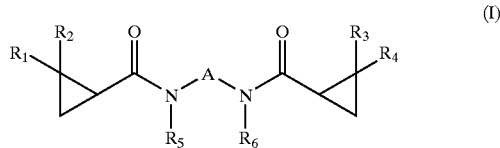

(I)

wherein R$_1$ to R$_4$, which may be the same or different from each other, each represent methyl group or chlorine atom, R$_5$ and R$_6$, which may be the same or different from each other, each represent hydrogen atom, an alkyl group having 1 to 6 carbon atoms or an aryl group which may have a substituent(s), and —A— represents one of the groups of the following general formulae (ii), (iii), (iv) and (v):

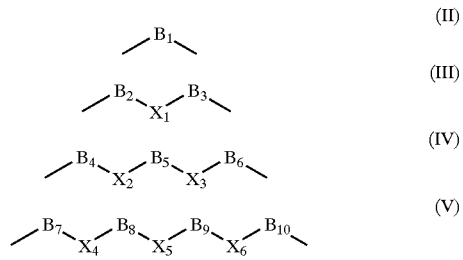

wherein B$_1$ to B$_{10}$, which may be the same or different from each other, each represent an aromatic ring which may have a substituent(s) or an aromatic heterocyclic group having at least one hetero atom, which may have a substituent(s), —X$_1$— to —X$_6$—, which may be the same or different from each other, each represent an interatomic bond, —O—, —NR$_7$—, —CR$_8$R$_9$—, —S—, —SO—, —SO$_2$—, —CO—, —O—CO—, —CO—O—, —NR$_{10}$—CO—or —CO—NR$_{11}$—wherein R$_7$ represents hydrogen atom, an alkyl group having 1 to 6 carbon atoms or an acyl group having 1 to 6 carbon atoms, R$_8$ to R$_9$ each represent hydrogen atom, hydroxyl group, a halogen atom, an alkyl group having 1 to 6 carbon atoms or an alkoxyl group having 1 to 6 carbon atoms, and R$_{10}$ to R$_{11}$ each represent hydrogen atom or an alkyl group having 1 to 6 carbon atoms,
with the proviso that when —A— is represented by the general formula (III), at least one of B$_2$ and B$_3$ cannot be benzene ring.

2. The biscyclopropanecarboxamide compounds and pharmaceutically acceptable salts thereof according to claim 1, wherein $R_5$ and $R_6$ in the general formula (I) each represent hydrogen atom.

3. The biscyclopropanecarboxamide compounds and pharmaceutically acceptable salts thereof according to claim 1, wherein $R_5$ and $R_6$ in the general formula (I) each represent hydrogen atom, and $B_1$, $B_2$, $B_4$ and $B_7$ in the general formulae (II), (III), (IV) and (V), respectively, represent benzene ring which may have a substituent(s).

4. The biscyclopropanecarboxamide compounds and pharmaceutically acceptable salts thereof according to claim 1, wherein $R_5$ and $R_6$ in the general formula (I) each represent hydrogen atom, and $B_1$ to $B_{10}$ in the general formulae (II), (III), (IV) and (V) each represent benzene ring which may have a substituent(s).

5. The biscyclopropanecarboxamide compounds and pharmaceutically acceptable salts thereof according to claim 1, wherein $R_5$ and $R_6$ in the general formula (I) each represent hydrogen atom, and —A— represents the following general formula (VI) or (VII):

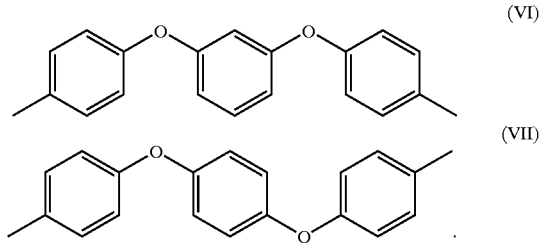

(VI)

(VII)

6. The biscyclopropanecarboxamide compounds and pharmaceutically acceptable salts thereof according to claim 1, wherein $R_5$ and $R_6$ in the general formula (I) each represent hydrogen atom, and —A— represents benzene ring which may have a substituent.

7. The biscyclopropanecarboxamide compounds and pharmaceutically acceptable salts thereof according to claim 1 wherein, in general formula (I), $R_1$ to $R_4$ each represent methyl group, $R_5$ and $R_6$ each represent hydrogen atom, and —A— represents benzene ring having a substituent(s).

8. The biscyclopropanecarboxamide compounds and pharmaceutically acceptable salts thereof according to claim 1 wherein, in general formula (I), the absolute configuration of the two carbon atoms each connected to the carbonyl group on the cyclopropyl group in general formula (I) is S.

9. The biscyclopropanecarboxamide compounds and pharmaceutically acceptable salts thereof according to claim 1 wherein, in general formula (I), the absolute configuration of the two carbon atoms each connected to the carbonyl group on the cyclopropyl group in general formula (I) is R.

10. A pharmaceutical composition containing the biscyclopropanecarboxamide compound(s) or pharmaceutically acceptable salt(s) thereof according to claim 1.

11. The pharmaceutical composition according to claim 10, wherein $R_5$ and $R_6$ in the general formula (I) each represent hydrogen atom, and —A— represents the following general formula (VI) or (VII):

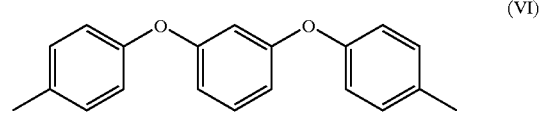

(VI)

(VII)

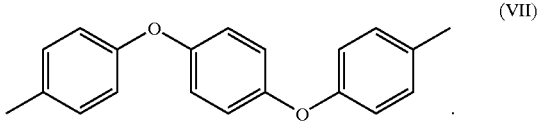

12. An NF-kappa B activation inhibitor containing the biscyclopropanecarboxamide compound(s) or pharmaceutically acceptable salt(s) thereof according to claim 1 as the active ingredient.

13. The NF-kappa B activation inhibitor according to claim 12, wherein $R_5$ and $R_6$ in the general formula (I) each represent hydrogen atom, and —A— represents the following general formula (VI) or (VII):

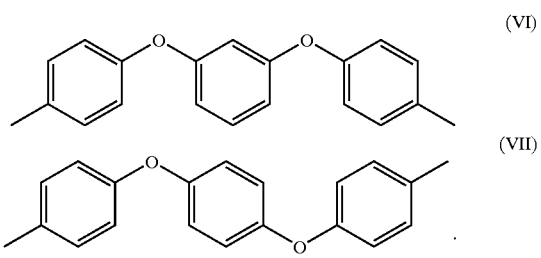

(VI)

(VII)

14. An inflammatory cytokine production inhibitor, a matrix metalloprotease production inhibitor and an inhibitor of incidence of inflammatory cellular adhesion factors containing the biscyclopropanecarboxamide compound(s) or pharmaceutically acceptable salt(s) thereof according to claim 1 as the active ingredient.

15. An inflammatory cytokine production inhibitor, a matrix metalloprotease production inhibitor and an inhibitor of incidence of inflammatory cell adhesion molecules inhibitor according to claim 14, wherein $R_5$ and $R_6$ in the general formula (I) each represent hydrogen atom, and —A— represents the following general formula (VI) or (VII):

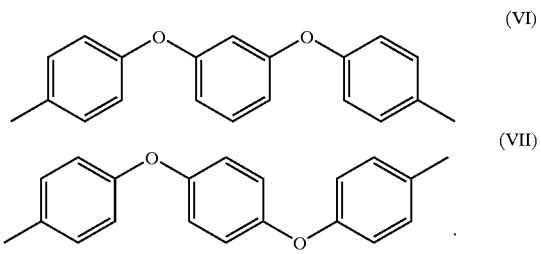

(VI)

(VII)

16. An antiinflammatory agent, an antirheumatic agent, an immunosuppressive agent, a cancerous metastasis inhibitor or an antiviral agent containing the biscyclopropanecarboxamide compound(s) or pharmaceutically acceptable salt(s) thereof according to claim 1 as the active ingredient.

17. The antiinflammatory agent, an antirheumatic agent, an immunosuppressive agent, a cancerous metastasis inhibitor or an antiviral agent according to claim 16, wherein $R_5$ and $R_6$ in the general formula (I) each represent hydrogen atom, and —A— represents the following general formula (VI) or (VII):

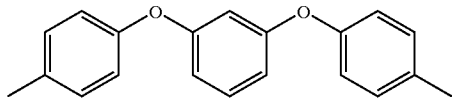 (VI)
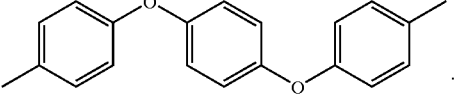 (VII)
* * * * *